(12) United States Patent
Johanson (10) Patent No.: US 8,467,066 B2
(45) Date of Patent: Jun. 18, 2013

(54) MIXTURE SEGREGATION TESTING DEVICES AND METHODS

(75) Inventor: Kerry Johanson, Gainesville, FL (US)

(73) Assignee: Johanson Holdings LLC, Gainesville, FL (US)

( * ) Notice: Subject to any disclaimer, the term of this patent is extended or adjusted under 35 U.S.C. 154(b) by 162 days.

(21) Appl. No.: 13/059,404

(22) PCT Filed: Sep. 11, 2009

(86) PCT No.: PCT/US2009/056695
§ 371 (c)(1),
(2), (4) Date: Feb. 16, 2011

(87) PCT Pub. No.: WO2010/036523
PCT Pub. Date: Apr. 1, 2010

(65) Prior Publication Data
US 2012/0033199 A1 Feb. 9, 2012

Related U.S. Application Data

(60) Provisional application No. 61/194,585, filed on Sep. 29, 2008.

(51) Int. Cl.
*G01N 21/55* (2006.01)

(52) U.S. Cl.
USPC .......................................... 356/445; 356/300

(58) Field of Classification Search
USPC ................... 356/432–440, 445–448, 300, 301
See application file for complete search history.

(56) References Cited

U.S. PATENT DOCUMENTS

| | | | | |
|---|---|---|---|---|
| 4,054,384 | A | * | 10/1977 | Hawes ............................ 356/51 |
| 4,126,396 | A | | 11/1978 | Hartmann |
| 5,121,986 | A | | 6/1992 | Rutz |
| 5,363,052 | A | * | 11/1994 | McKee ......................... 324/663 |
| 6,316,772 | B1 | | 11/2001 | Egelberg |
| 6,418,805 | B1 | * | 7/2002 | Carney et al. .................. 73/866 |
| 6,595,678 | B2 | | 7/2003 | Folestad |
| 7,057,722 | B2 | | 6/2006 | Gehrlein |
| 2011/0101242 | A1 | * | 5/2011 | Dickens et al. ............ 250/459.1 |

* cited by examiner

*Primary Examiner* — Hao Pham
(74) *Attorney, Agent, or Firm* — Sven W. Hanson (57) ABSTRACT

Methods and devices are provided to measure segregation in solid particulate mixtures. Light energy is projected through a transparent barrier and reflected off a surface of a mixture volume. The constituent fraction in the mixture is determined by analyzing the mixture reflected light as a combination of the constituents' known reflected light spectral contents and intensities. This is accomplished at multiple surface locations to provide constituent fraction data over the mixture volume surface.

10 Claims, 9 Drawing Sheets

MIXTURE SEGREGATION TESTING DEVICES AND METHODS

RELATED APPLICATIONS

This application claims priority benefit from international application PCT/US2009/56695 filed Sep. 11, 2009 claiming priority from U.S. Provisional Application No. 61/194,585, filed Sep. 29, 2008.

BACKGROUND OF THE INVENTION

The present invention pertains to methods and device for testing or measuring segregation of constituents of a mixture of particulate solids. In particular, the invention are photometric methods and devices for measuring both the quantity and spatial dispersion of different particles in a mixture of various solid particles.

In a great variety of industries and technologies mixtures of solid materials are known to segregate. Segregation is relative movement of one or more of the different solid constituents within a mixture resulting in spatial stratification and non-uniformity within a volume of the mixture. Segregation can occur in previously uniform mixtures as a result of a variety of events or forces occurring in transportation and handling and are typically induced by differences in particles size, shape, density and other mechanical and chemical properties.

In process design, the solution to a segregation problem can be attacked from two angles. The process can be modified to accommodate segregation patterns caused by the various mechanisms or changes can be made to the process to reduce the cause of segregation. In either case, understanding segregation mechanisms is critical to developing robust processes to handle segregating materials.

Materials segregate when handled for a variety of reasons. Many solids flow practitioners quickly identify the potential for fine material to sift through the matrix of coarse particles as material slides down a pile. Indeed, sifting segregation is a predominant cause of separation during handling of differently sized particles. This mechanism usually results in a radial segregation pattern where fines accumulate near the center of a pile while the coarse material is predominately at the pile's edge. However, severe sifting segregation can cause a top-to-bottom segregation pattern where the fines are beneath the coarse particles. This is especially true if inter-particle motion is induced within the material by some external means such as vibration. Typically, particle size differences greater than three to one are enough to produce significant sifting segregation problems.

As well, some particles have differences in inter-particle friction and thus form piles with different repose angles. Formation of piles within process equipment causes the less frictional particle to slide further down the pile accumulation at the pile's edge. This mechanism results in a radial segregation pattern. Materials with an angle of repose difference of more than 2 degrees can show significant repose angle segregation.

Air currents caused during filling may carry fine material to regions where the air currents decrease sufficiently to deposit the fine material. This air entrainment segregation can produce a radial pattern or a side-to-side pattern depending on the position of the inlet and the geometry of the vessel. Generally, fines accumulate near process vessel walls with this segregation.

Other events can also result in segregation of materials within. Segregation is a problem because of the resulting uncertainty and or nonuniformity of the materials when applied or used in processes. In a simple example: segregation of bulk mixtures of baking ingredients in industrial food production can result in significant loss of quality control.

Knowing the segregation mechanism as well as the flow profiles in process equipment is critical to solving segregation problems. In typical existing segregation test methods, mixture samples are taken from process streams of material, and the constituents physically measured, in order to learn the segregation parameters. However, these methods are limited in application and inaccurate. Methods of accurately measuring the magnitude and type of segregation occurring in material process systems are needed.

SUMMARY OF THE INVENTION

The present invention is methods and devices for photometrically measuring the constituents of a segregated mixture of materials. In the inventive methods a known light source is reflected off the surface of a volume of a mixture. The reflected light is detected and measured. The spectral content of the reflected light is at least partially a result of physical and chemical properties of each and all of the individual constituents of the mixture. The properties of reflected light of each constituent alone are also determined. The constituent fraction in the mixture is determined by analyzing the mixture reflected light as a combination of the constituent's known reflected light spectral content and intensity. This is accomplished at multiple surface locations to provide constituent fraction data over the mixture volume surface. This data defines segregation within the volume.

Devices are provided that induce segregation in a material of interest in a configuration that forms a convenient volume surface for measuring the desired segregation. In various embodiments, the device mimics or reproduces a process flow geometry or flow pattern or flow event of interest while forming a test volume surface for measuring segregation according to the inventive methods.

DESCRIPTION OF THE EMBODIMENTS

Figure 1A:
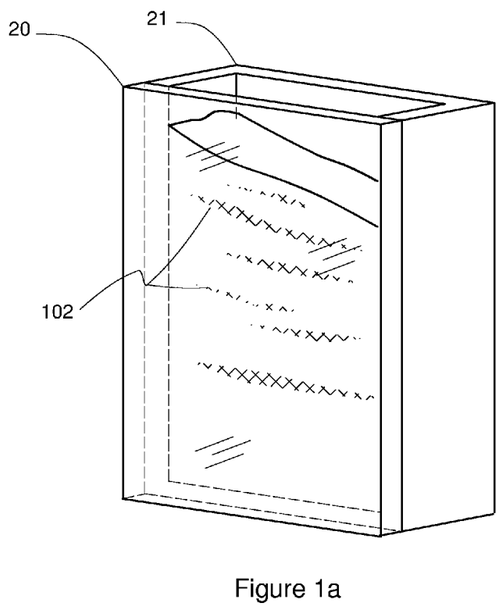
FIGS. 1a and 1b illustrate, in perspective and cross section views, a segregated mixture contained behind a photometrically transparent barrier according to the invention.
Figure 1B:
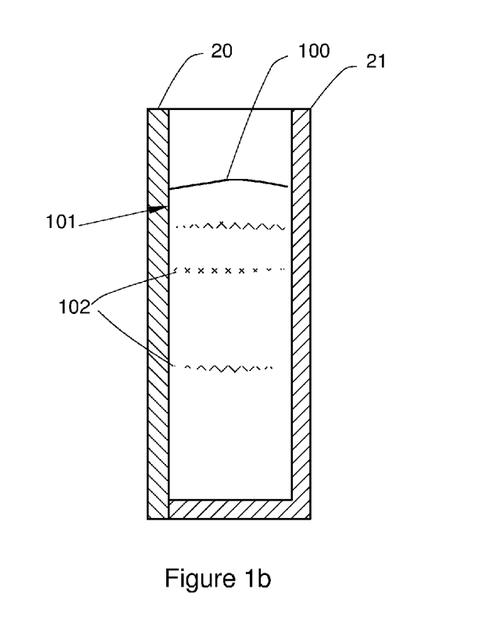

FIGS. 1a, 1b illustrate a segregated mixture contained behind a photometrically transparent barrier 20 according to the invention. To enable obtaining data, a mixture of interest is retained as a stationary volume 100 bounded by a photometrically transparent barrier 20. Herein, the term "photometrically transparent" or more simply "transparent" means a barrier that allows transmission of light within a specified or known spectrum without appreciable absorption at any wavelength within the spectrum.

In the figures, the mixture volume 100 is retained within a closed container 21 incorporating the transparent barrier 20. In some applications, a closed container 21 may not be necessary so long as the proper mixture segregation can be obtained in the volume 100 with respect to the barrier 20. The mixture volume 100 is formed such that segregation in the mixture at the surface 101 of the volume 100 adjacent the barrier 20 is representative of a mixture and process of interest. Volume regions of segregated constituent particles 102 are shown differentiated from other particles in the volume 100.

Figure 2A:
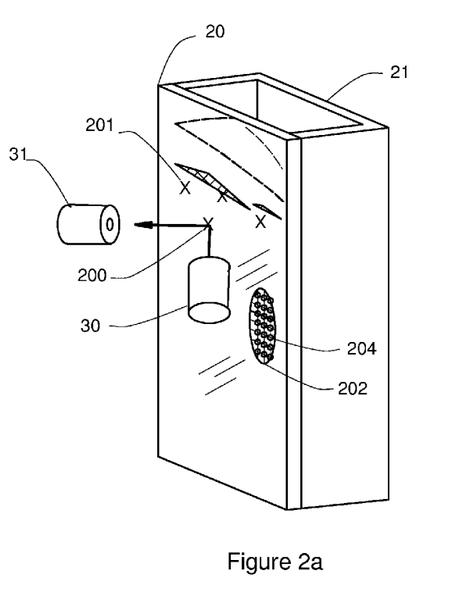
FIGS. 2a and 2b depict, in perspective and horizontal cross-section views, a method of obtaining segregation light reflective data from a mixture volume according to the invention.
Figure 2B:
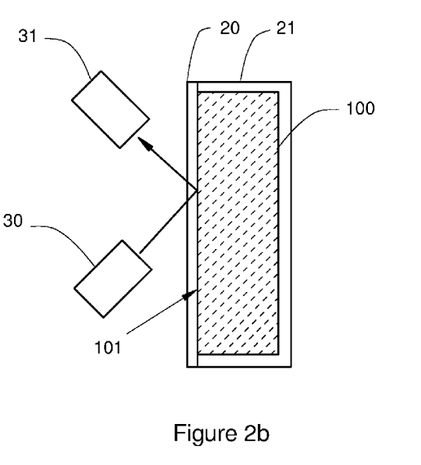

FIGS. 2a and 2b show the same container 21 and volume 100 as in FIGS. 1a, 1b. An inventive method step of obtaining reflective data from the mixture volume 100 is illustrated. A light source 30 is aligned at a fixed angle and distance from the barrier 20. Light is projected from the source 30, through the barrier 20, and at least partially reflected back through the barrier 20 to be detected by a detector 31. The detector 31 is also at a fixed angle and distance from the barrier 20. The light source 30 is selected and configured to illuminate only a surface area of predetermined limited size, at a known location 200 of the surface. The source 30 and detector 31 are both together moved to sequentially illuminate, and detect, light reflected from multiple further known locations 201 over the surface 101. In this manner, reflected light data may be obtained at various points over the surface of a mixture volume. Constituent data from the multiple points provides indications or measures of segregation.

For simplicity, in FIGS. 2a and 2b the light is shown as a one-dimensional line. In fact, the light may be projected from the source 30 as a column or as a divergent beam illuminating the surface 101. The shape of the illuminated area of the surface 101 is not critical. However, the size of the illuminated area must be large enough to include a locally representative sample of constituents. The minimum size is dependent on the size and fraction of the constituent particles. The maximum is dependent on the resolution that is needed to define the segregation. A minimum area of illumination with a diameter (nominal width) of at least five (5) times the largest particle diameter has been found to be effective in most applications. Alternatively, a view port 202 of the same size may be defined for illumination at multiple distinct and representative points 204 within the viewport 202. The obtained spectra at the multiple points 202 may be averaged to determine the effective spectra of the viewport 204.

To limit error, the distance between the detector 31 and the illuminated area is preferably maintained at no greater than 25 (twenty five) times the diameter dimension of the detector aperture. This is somewhat a function of illumination intensity, but increased illumination intensity may reduce the ability to differentiate variations in constituent spectral intensities.

Figure 3:
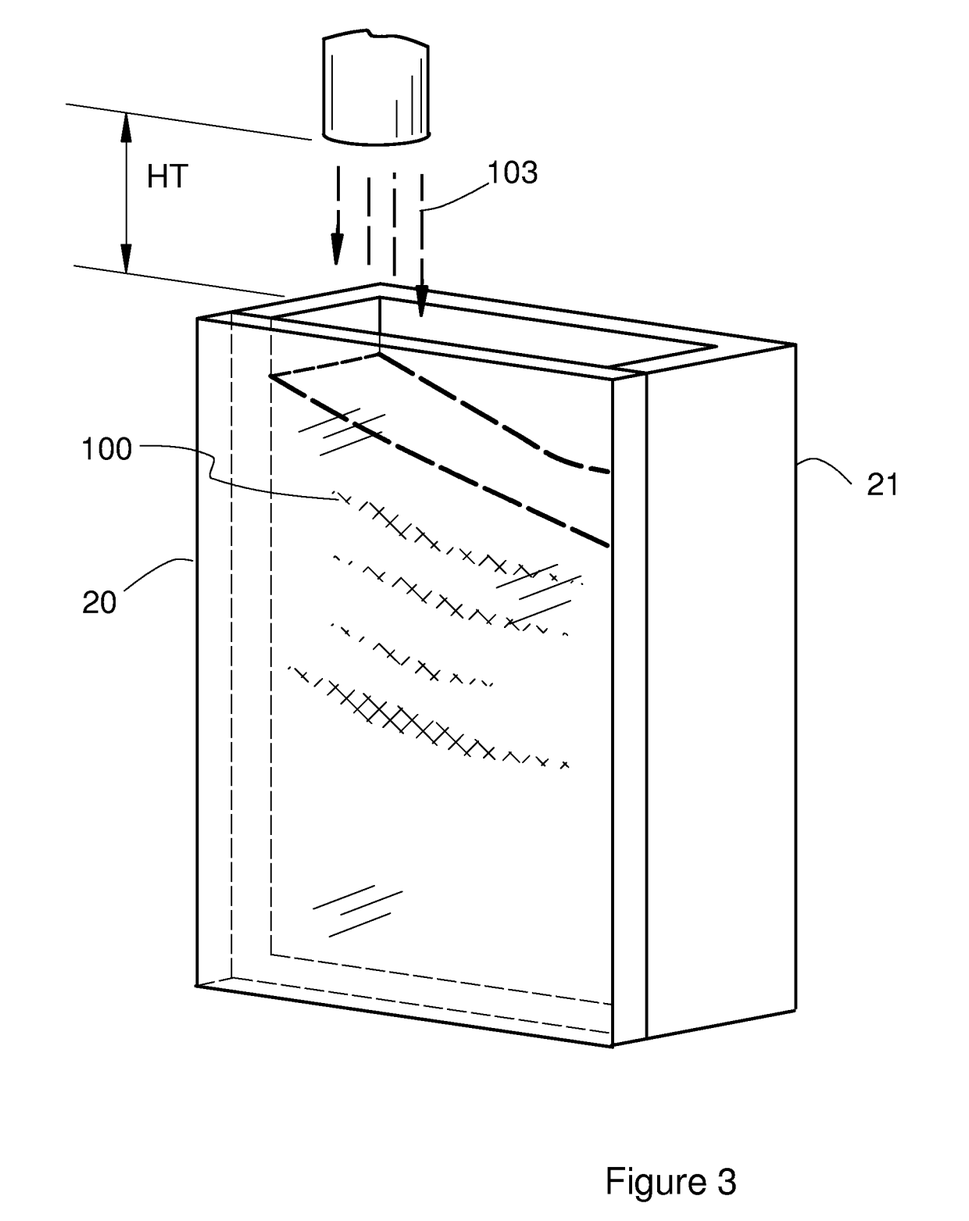
FIG. 3 illustrates forming a segregated mixture including a selected test process before obtaining segregation reflective data.

In FIG. 3, an alternative configuration of a mixture volume 100 is formed in an inventive method step of introducing the constituents 102 into a container 21 using a selected physical process: here, for example, allowing a mixture 103 of constituents to fall freely from selected height HT to form a volume 100 with a natural angle of repose. This example is not limiting, but is shown as a manner to illustrate the inventive concepts. In other applications, the physical processes may be selected to mimic the anticipated parameters of an application process that is desired to be controlled to achieve, prevent or control certain segregation events or results. For example, the speed of constituent movement, agitation, height of fall, air currents, static electric buildup, shape and size of conduit or container, and other parameters, may each independently or together effect or induce segregation in a particular process and so might be mimicked in various particular alternative applications of the inventive device and system to obtain useful segregation data.

Figure 4:
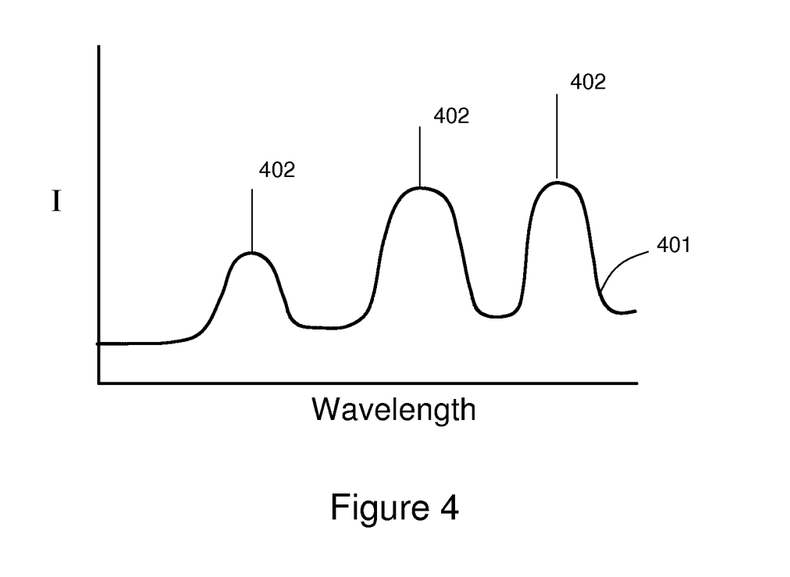
FIG. 4 is an example data set of reflective light energy as a continuous graph of intensity versus wavelength as produced in the inventive methods.

As discussed above, reflective light data are acquired at representative locations over a mixture volume surface. The analysis of this data to determine constituent makeup is now described in the following. The light data from each surface location 200, 201 (FIG. 2a) consists of a representation of light reflected energy intensity values as a function of wavelength. This is illustrated in one form of data set, in FIG. 4, as a continuous graph 401 of intensity versus wavelength. This data set may also be defined by tabulated intensity values for discrete wavelengths or wavelength bands. Each location 200, 201 will have a distinct such representation or data set. FIG. 4 illustrates the phenomena typically observed: that reflective light of constituents occurs at distinct wavelengths resulting in peaks 402 on a graph of intensity over wavelength.

In alternative methods of defining constituent spectra, spectra curves may be represented by first and second moment (derivatives), or by subtracting the measured spectra from any linear combination of pure component spectra, and the respective spectral curve wavelengths.

Figure 5:
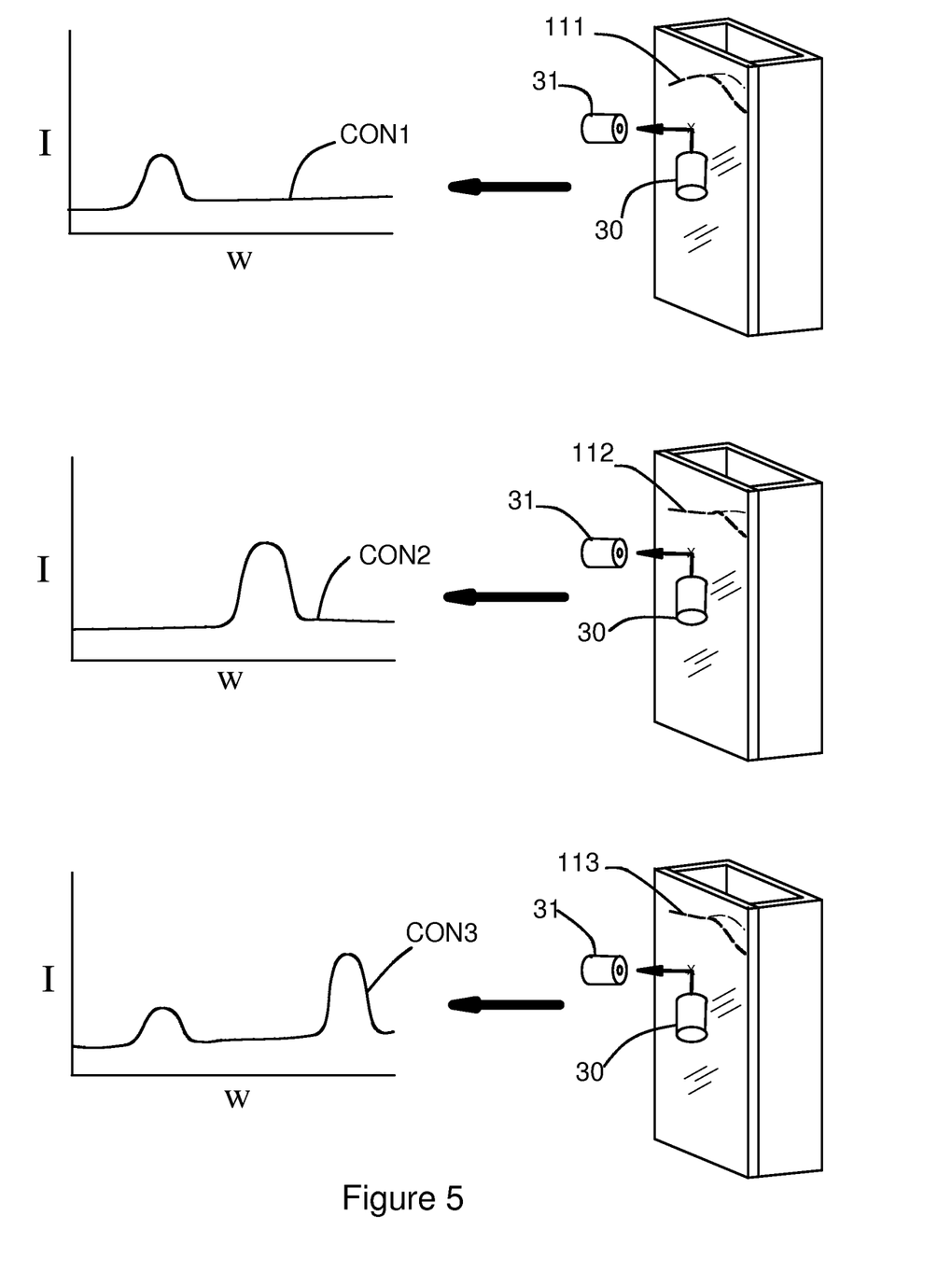
FIG. 5 illustrates the inventive method step of obtaining signature reflective light data for multiple known constituents.

To determine the constituent makeup of the mixture, the contribution of each constituent to the total reflected light energy is determined. An essential step is obtaining a "signature" spectrum of reflected light for each constituent. This step is illustrated in FIG. 5 where individual constituent volumes 111, 112, 113 are formed of each of the different pure constituent materials that are to be resolved. In this example, there are three constituents, but it should be understood that the number of different constituents are not limited. In the manner discussed above, a light source 30 and detector 31 are used to obtain reflective light intensity data for each constituent volume. The various different data sets for the associated constituents are illustrated by the resulting graphs CON1, CON2, CON3 of light intensity versus wavelength for the three respective constituents. The differences in the spectral contents of the constituents are a function of one or more of a number of physical and chemical parameters including, but not limited to: particle size and shape, chemical composition, porosity, water content, and others both known and possibly unknown. For example, the intensity of the reflected light from sugar particles is dependent on the grain size: a volume of fine-grained sugar will reflect more intense light that will sugar of larger size grains. It should be noted that the graphs differ in the location and, or, height of their identifying peaks.

A basic presumption of the inventive methods and operation of the devices is that the contribution of each constituent's reflective light energy to the total mixture reflective light energy is proportional to a monomodal function of the fraction of the constituent in the mixture. After all the constituent signature data are obtained (as depicted in FIG. 5), the constituent makeup of each subject mixture surface location is calculated independently, using the reflective data set for that location. This is accomplished by use of a constrained, linear curve fitting analysis using least squares method to determine the fractional contribution of each constituent. The analysis method is well known in other applications, and once the above data is provided, and the desired solution form known, the appropriate analysis method steps will be clear to those familiar with curve fitting and least squares analysis. All constituent fractions are constrained for the analysis to values between zero and 1.0 (the value one), and the sum of the fractions must also equal 1.0.

The result of analysis of the light data is values of fractions of each constituent at the associated mixture surface location. Obtaining data, and analyzing the data, at multiple locations over an area of a volume surface will provide a collection of constituent fractions over the surface. This data may be presented using any of a variety of means or methods such as statistical data representing overall segregation, graphical representations of the entire data collection, or other methods as needed in specific applications.

Figure 6:
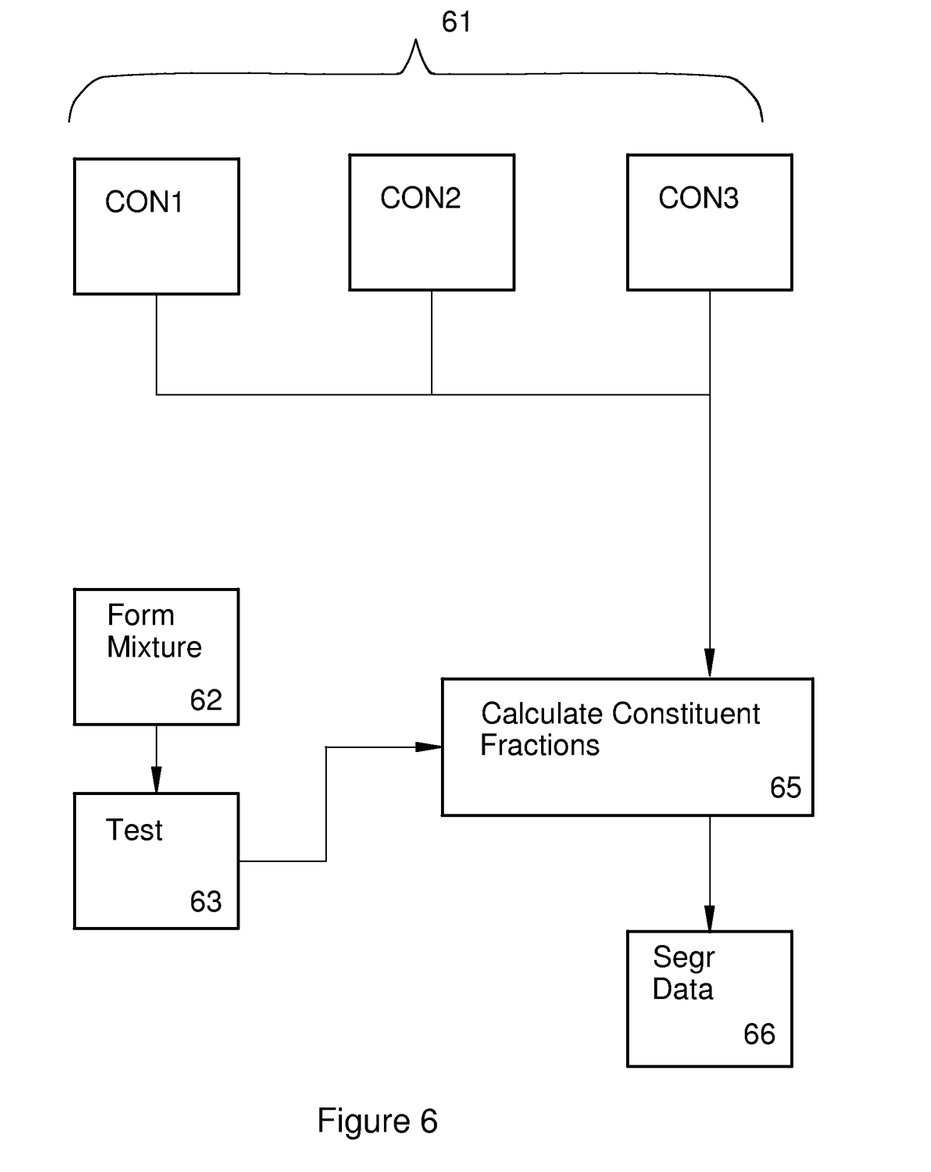
FIG. 6 is a schematic diagram of one embodiment of the general method steps.

For further explanation, FIG. 6 provides a schematic diagram of one embodiment of the general method steps. At the top, signature reflective data for each of multiple constituents CON1, CON2, CON3 are obtained 61 as discussed above. In the diagram, three constituents are shown; but as discussed above, the number of distinct constituents may be any number greater than one. A volume of the mixture of interest is formed 62 while allowing or inducing segregation processes or events to occur. Reflective light data from multiple selected mixture surface locations is obtained in a test step 63. The surface points or viewports to be used to obtain test data may be accomplished on an ad hoc basis determined by empirical knowledge of segregation, or may the test area and points may be preselected and test operations automated.

The step of obtaining constituent signature data 61 may occur in any sequence with the steps of mixture forming 62 and testing 63. Once the reflective light data is available, constituent fractions are calculated 65 at each location. As discussed, this may be accomplished by use of mathematical curve fitting methods, or other methods of accomplishing the same result. From this data, segregation data is formed 66. This step may include any of a variety of methods, including calculating a single numeric segregation indicator, generating graphical representations of constituent fractions, or generating other forms of segregation data sets.

Figure 7A:
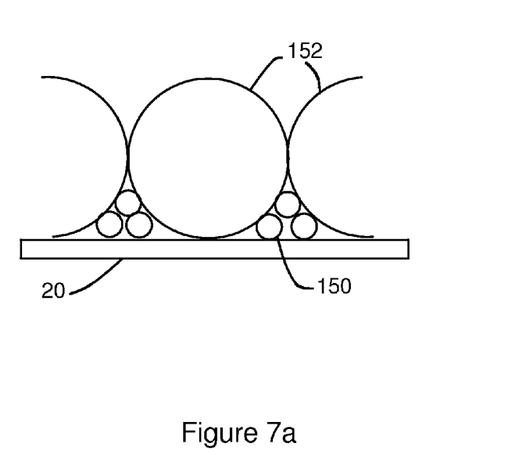
FIGS. 7a and 7b are top and side views of fine and coarse particles in a mixture used to illustrate nonlinear coverage.
Figure 7B:
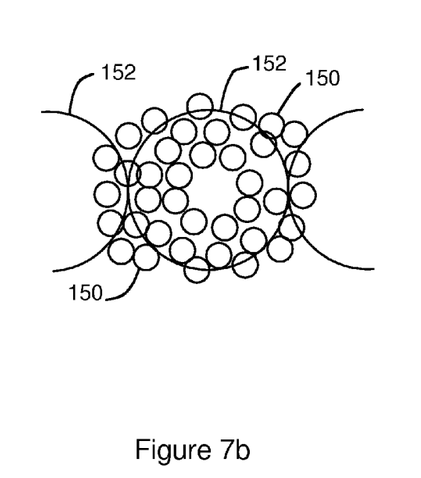

The spectra of a mixture of two or more different materials is linearly additive based on area exposed to, and reflecting the illuminating light energy. However, in cases of significantly different size particles, the smaller size particles can coat the coarse particles or fill the voids in between coarse particles. In either case, the area of the coarse particles exposed is blocked by fine particles. This effect is non-linear based on the volume ratios of different particles in the system. The detector sees reflected light predominantly from the more fine particles than the volume ratio the sample would suggest. This is illustrated in FIGS. 7a and 7b in which fine particles 150 fill in voids between larger particles 152.

In such cases, to enable the calculation of individual concentrations in the mixture from spectral data collected from the pure components and local mixtures, a modified weighted average of the spectral data can be used to compute the concentration in the segregation tester. If enough data points are taken across the test mixture surface, the total average pure component concentrations measured within the mixture will equal the target mixture concentrations placed within the segregation tester. For example, if the mixture volume actually consists of 30 percent red particles, 60 percent blue particles and 10 percent yellow particles, then local mixture spectra are scaled such that the weighted averages of spectral data at each sample mixture point would provide a deviation off of these overall averages.

The spectral data of N pure components can be combined to provide an estimate of the concentration within a mixture of these pure components according to Equation 1:

$$\lambda \text{mix}_{j,k} = \sum_{i=1}^{npure} W_i \times f_{i,j} \times \lambda_{i,k} \qquad (1)$$

Where:
$W_i$ is the weight function for the $i^{th}$ pure component
$f_{i,j}$ is the spectral fraction for the $i^{th}$ pure component and the $j^{th}$ measurement point.
$\lambda \text{mix}_{j,k}$ is the mixture spectral intensity at the $k^{th}$ wavelength and the $j^{th}$ measurement point
$\lambda_{i,k}$ is the spectral intensity of the $i^{th}$ pure component and the $k^{th}$ wavelength.

The function G, shown in Equation 2, is minimized to provide a least squares estimate of the mixture curve fit using $w_i$ and $f_{i,j}$ as curve fit parameters:

$$G = \sum_{k=1}^{n\lambda} \sum_{j=1}^{npts} (\lambda \text{mix}_{j,k} - \sum_{i=1}^{npure} W_i \times f_{i,j} \times \lambda_{i,k})^2 \qquad (2)$$

However there are several constraints that must be satisfied during this minimization procedure. One of these constraints suggests that the sum of weighted fraction for any $i_{th}$ component equals the global average concentration $\text{Cavg}_i$ placed in the segregation tester. This is expressed, for all i pure components, in Equation 3:

$$\text{Cavg}_i = \sum_{j=1}^{npts} W_i \times f_{i,j} \qquad (3)$$

The local sum of all weighted fractions for any $j^{th}$ measurement point must also equal 1. This constraint is expressed, for all j measurement points, in Equation 4 below.

$$\sum_{i=1}^{npure} W_i \times f_{i,j} = 1 \qquad (4)$$

Equations 2, 3, and 4 are then solved using standard techniques for nonlinear least squares with general constraints. The solution of these equations gives the concentration of pure components at each measurement point and provides the data needed for determining the segregation profile in the spectral segregation tester.

Figure 8:
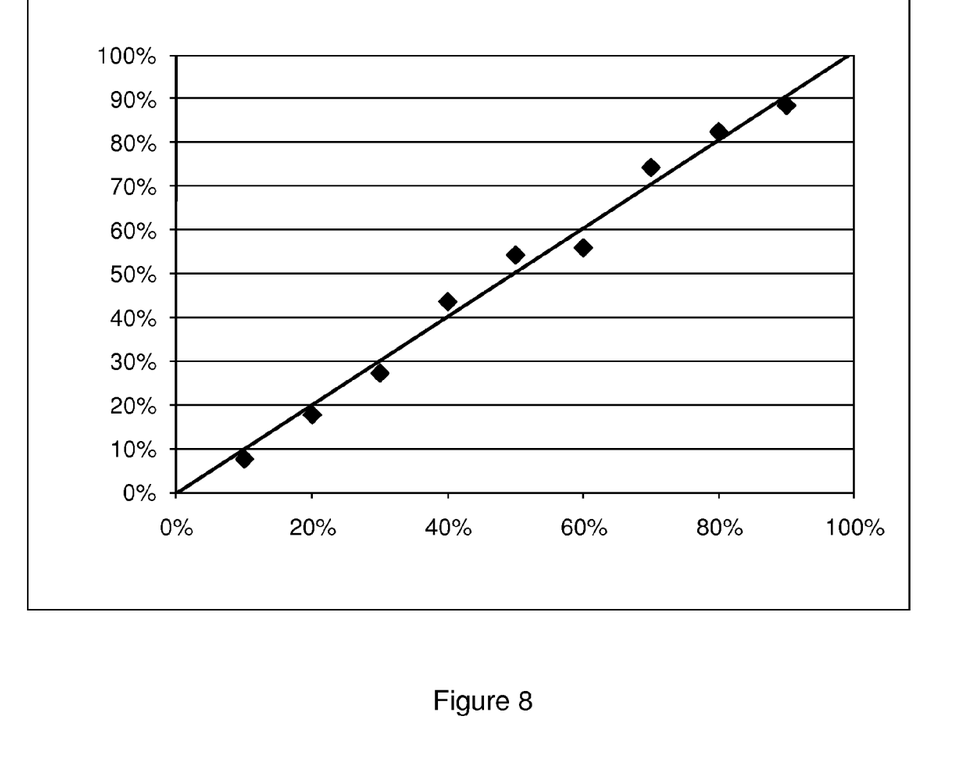
FIG. 8 is a graph of a mixture constituent fraction as determined by the inventive methods plotted against a known fraction, in a test of the method theory basis.

The general inventive methods were tested by applying the above methods to various known uniform mixtures of granular baking sugar and a chocolate-based particulate material designed for use in baking decoration. The two constituents differ at least in their respective chemical composition, and particle shape, size and color. Signature reflective light data was obtained for both materials contained behind a glass barrier. Several different mixtures of the two constituents were formed, each with a different constituent fractional makeup. A reflective light data set for each mixture was then obtained in the manner described above. The constituent makeup was then calculated as described above. FIG. 8 is a graph of the result: the calculated percentage of chocolate particulate "sprinkles" is plotted (vertical axis) against the known or actual value (horizontal axis). The diagonal line reflects the zero error solution. The minimal error in the calculated values are acceptable in most industrial applications where segregation data is valuable.

Figure 9:
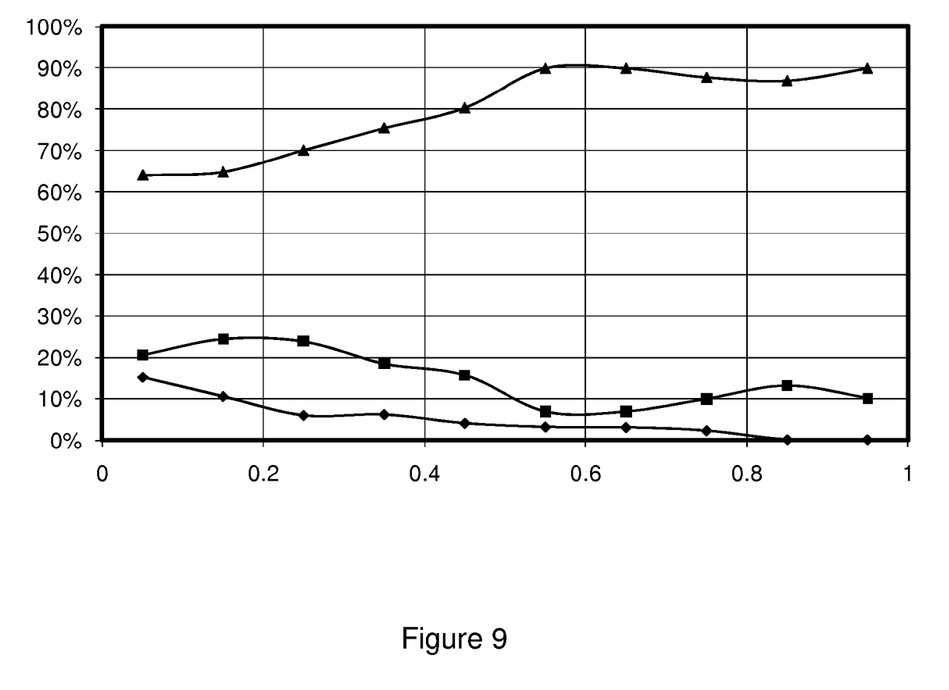
FIG. 9 is a graph of test data of mixture constituent concentration, in solid mixture of three constituents, as calculated by the inventive method over a volume area.

FIG. 9 presents segregation data obtained from using the above inventive method steps to analyze a solid mixture of the three constituents: ground cinnamon, sugar, and rolled oatmeal, as representative of a consumer cereal mixture for human consumption. A segregated volume of the mixture was formed with average constituent makeup of: 5 percent cinnamon, 15 percent sugar, and 80 percent rolled oats. Constituent concentrations were determined by the inventive methods at various distances, vertically, in the volume. The concentration percentage data for each constituent are plotted in FIG. 9 as a function of dimensionless location (horizontal axis) from the top (0) to the bottom (1.0) of the mixture volume. The variation of each line from the average for that constituent represents segregation. It should be noted that in this example test, the rolled oats particles are many times the nominal size of the cinnamon and sugar particles. That the average of the calculated data equals the known constituent makeup is verification of the present methods in such conditions.

Generally in the inventive method and devices, before measurement of light intensity, the reflected light must be separated into spectral components. This may accomplished with a grating or prism or other standard optical devices for providing the same result or function. After separation, the reflected light is allowed to fall on, or is directed to, a light energy measuring device having the appropriate intensity and wavelength sensitivity. These functions may be provided by conventional laboratory spectrometers designed for similar purposes.

In FIG. 2b, the light source is shown directed at the volume 100 at a non-zero angle of incidence with the surface. This is preferred to prevent specular reflection from the surface of the barrier 20. The angle of incidence is not critical otherwise. The light is reflected diffusely from the surface 101, such that the particular orientation and placement of the detector 31 is not critical so long as the distance from the detector 31 to the surface 101 is constant and allows reception of sufficient light energy.

The light source 30 must be selected to provide light including the reflective wavelength spectrum of all of the constituents of interest. For most applications, a convenient light source provides light with a spectrum including the range of 200 to 1100 nanometers. The light energy of the light source may include light energy outside this spectrum range. The transparent barrier 20, likewise, need not be transparent to light outside of the wavelength range used to identify the constituents.

In variations of the inventive methods, the mixture volume 100 is not formed to simulate an external process or mixture. Rather, constituents may be mixed and selected process steps followed to form a mixture volume, and segregation data obtained, to provide standardized segregation data relating to selected constituents.

Once the signature spectrum of one or more constituents are obtained, the signatures may be used in future mixture analysis where the same constituent is present in a mixture. A new signature need not be obtained so long as the constituent material remains constant. If any parameter of the constituent material that might effect light reflectivity changes, a new signature may be necessary. For example, sugar used in baking processes are available in various size granules and each would have a distinct signature.

In distinct applications, segregation data of one, or a subset, of all the constituents may be the desired information. In such cases, after analysis of the fractions of all constituents, it may be desirable to form a final data set representing only fraction data for one, or a subset, of all constituents.

The above methods may be carried out using any of a variety of structures and devices for manipulating mixtures and obtaining the reflective light data as required.

To make the inventive device more useful in a commercial setting, reflective data may be obtained in a more automated fashion. For example, the illuminating and detecting devices may be mounted on moveable structures and automatically indexed to collect spectra at multiple positions over a surface for use in analysis.

The invention claimed is:

1. A method for measuring segregation of two or more particulate constituents in a mixture comprising:
    forming a stationary mixed volume of two or more different particle constituents;
    directing light onto a first location on a surface of the volume;
    measuring the light intensity reflected from the surface at various different wavelengths;
    determining the fraction of each constituent from their respective measured light intensities and constituent signature spectrums; and
    repeating the directing, measuring, determining steps at a multiple of further different locations on the surface.

2. A method, according to claim 1, and further comprising:
    forming the volume of constituents against a transparent barrier; and
    directing the light through the barrier.

3. A method, according to claim 1, and further comprising:
    obtaining a respective signature spectrum for each constituent by illuminating
    respective pure volumes of each constituent with a common light source and
    measuring the reflected light for each.

4. A method, according to claim 1, and further comprising:
    separating the reflected light into different wavelengths before measuring the light energy at each wavelength.

5. A method, according to claim 1, and wherein:
    the light directed onto the volume comprises light having a wavelength in the range of 200 to 1100 nanometers.

6. A method, according to claim 1, and wherein:
    illuminating an area, at each location, having a diameter at least five times the largest constituent particle diameter.

7. A method for measuring segregation of two or more particulate constituents in a mixture comprising:
    forming a stationary volume of two or more different particulate constituents;
    directing light onto multiple locations on a surface of the volume;
    at each location measuring the light reflected at various different wavelengths from a locally representative sample of constituents;
    obtaining a respective signature spectrum for each constituent; and
    determining a respective fraction of each constituent for each location from the measured light intensities and constituent signature spectrum.

8. A method, according to claim 7, and wherein:
    in the step of directing light onto multiple locations, at each location the light is directed onto a surface area having a diameter of at least five times the size of the largest constituent particle.

9. A method for measuring segregation of two or more particulate constituents in a mixture comprising:
    allowing a mixture of multiple different particulate constituents to form a stationary volume surface;
    directing light onto a multiple of surface locations;
    obtaining unique light spectrum data for each of the constituents; and
    at each surface location: measuring the light intensity reflected from the surface at various different wavelengths and determining the fraction of each constituent at each location.

10. A method, according to claim 9, and further comprising:
    controlling the constituents prior to forming the stationary volume such that the stationary volume is formed to mimic a selected process result.

* * * * *